United States Patent [19]

Degani et al.

[11] 4,449,004

[45] May 15, 1984

[54] PROCESS FOR PREPARING ORGANIC SULPHIDES

[75] Inventors: Iacopo Degani; Rita Fochi; Valeria Regondi, all of Turin, Italy

[73] Assignee: Consiglio Nazionale Delle Ricerche, Rome, Italy

[21] Appl. No.: 368,293

[22] Filed: Apr. 13, 1982

[30] Foreign Application Priority Data

Apr. 17, 1981 [IT] Italy ................................ 21263 A/81

[51] Int. Cl.³ ............................................ C07C 148/00
[52] U.S. Cl. ........................................ 568/38; 252/45; 568/59; 568/60; 544/210; 548/165
[58] Field of Search ...................... 252/45, 31; 568/38, 568/59, 60; 544/210; 548/165

[56] References Cited

U.S. PATENT DOCUMENTS

| 2,110,281 | 3/1938 | Adams et al. | 252/45 |
| 4,080,302 | 3/1978 | Davis et al. | 252/45 |
| 4,148,737 | 4/1979 | Liston et al. | 252/45 |

*Primary Examiner*—Jacqueline V. Howard
*Attorney, Agent, or Firm*—Young & Thompson

[57] ABSTRACT

A process for preparing organic thioethers of formula R—S—R₁ in which R is an aliphatic, aryl, arylaliphatic or heterocyclic radical and R₁ is an aliphatic or arylaliphatic radical, from organic dithiocarbonates and organic halides or sulphonates, in the presence of an aqueous alkaline base and a phase transfer catalyst, at a temperature of between 50° and 100° C. for a time of 10–60 minutes.

7 Claims, No Drawings

PROCESS FOR PREPARING ORGANIC SULPHIDES

BACKGROUND OF THE INVENTION

This invention relates to a new process for preparing organic sulphides, and more specifically for preparing aliphatic, aromatic, arylaliphatic and heterocyclic thioethers.

Thioethers are known industrially to constitute a large class of products used in many fields, for example as dyestuff and pharmaceutical intermediates, as pesticides, herbicides, oxidation inhibitors, additives for load-bearing lubricants and the like.

Because of the importance of this class of product, numerous processes have been proposed up to the present time for its preparation, these however being generally limited to the preparation of alkyl thioethers.

The most widely used industrial processes known up to the present day comprise:

1. Reacting an alkyl halide with a thiol in accordance with the equation:

$$R-X + YS-R_1 \rightarrow R-S-R_1 + XY$$

in which R is an alkyl group, $R_1$ is an aliphatic, aryl, arylaliphatic or heterocyclic radical, X is halogen, and Y is H or an alkali metal. According to one alternative the alkyl halide can be replaced by an alkyl sulphate; or 2. Reacting an alkyl mercaptan with an organic halide in accordance with the equation:

$$R-SH + X-R_1 \rightarrow R-S-R_1 + HX$$

in which R is an alkyl group, $R_1$ is an aliphatic, aryl, arylaliphatic or heterocyclic radical, and X is halogen.

Reaction (1) is generally used for preparing dialkyl sulphides or alkylaryl sulphides, whereas reaction (2) is most commonly used for preparing alkyl sulphides of heterocyclic compounds. Obviously, said reactions are carried out under very different operating conditions according to the specific reactants involved. In many cases, and in particular when $R_1$ is a heterocyclic radical, rather drastic temperature and pressure conditions and very long times are necessary. In addition, those processes which use alkyl mercaptans suffer from all the drawbacks which the use of such toxic and volatile compounds involves.

The present invention relates to a new extremely simple and economical process, which allows the industrial preparation, with high yields, in very short times and in the absence of solvents, of thioethers of formula:

$$R-S-R_1$$

in which R is an aliphatic, aryl, arylaliphatic or heterocyclic radical and $R_1$ is an aliphatic or arylaliphatic radical.

The process is of general character, and can be used for preparing practically any thioether included in the aforesaid formula, under substantially equivalent conditions.

SUMMARY OF THE INVENTION

The new process is characterised by reacting an organic dithiocarbonate with an organic halide or sulphonate in accordance with the equation:

$$2R-X + (R_1S)_2CO + H_2O \rightarrow 2R-S-R_1 + 2HX + CO_2 \quad (I)$$

in which:
R is an aliphatic, aryl, arylaliphatic or heterocyclic radical,
$R_1$ is an aliphatic or arylaliphatic radical,
X is Cl, Br, I, $-SO_3-CH_3$, or $-SO_3-C_6H_4-CH_3$.

Reaction (I) must be carried out in the presence of an aqueous alkali base and a phase transfer catalyst, heating to a temperature of between 50° and 100° C. The reaction time varies according to the reactants, but is generally of the order of 10-60 minutes, i.e. very short.

DESCRIPTION OF THE PREFERRED EMBODIMENTS

The starting substance are reacted either in the stoichiometric proportions required by equation (I) or with an excess of dithiocarbonate.

In all cases, it has been surprisingly found that when the substance R—X has been completely consumed, the excess dithiocarbonate is not decomposed to mercaptan by the alkaline base, but remains unaltered, and if necessary can be easily recovered from the reaction mixture.

When the reaction is complete, the organic phase essentially consists only of the thioether if the dithiocarbonate has been used in stoichiometric quantity and the catalyst is water-soluble. In such a case, the thioether can be isolated either by simple decantation, if liquid, or by filtration, if solid.

In this manner, the entire process can be carried out in the absence of solvents.

The crude thioether obtained in this manner can then be purified to the required degree by the usual crystallisation or distillation methods.

However, if the catalyst is liposoluble, the organic phase consists of the thioether and catalyst. In this case, after extracting the organic phase with a suitable solvent, the thioether can be freed from the catalyst either by filtering the solution through silica gel, which retains the catalyst, and then evaporating the solvent, or by previously evaporating the solvent and purifying the residue, either by crystallisation, or by distillation under vacuum.

The aqueous bases preferably used for carrying out reaction (I) are 30% NaOH and KOH. In this case, the effective progress of the reaction is represented by the following equation:

$$2R-X + (R_1S)_2 \xrightarrow[H_2O]{KOH} 2R-S-R_1 + 2KX + K_2CO_3 \quad (II)$$

As the reaction yield is practically quantative, the organic phase as stated consists practically only of the product $R-S-R_1$, sometimes accompanied by the catalyst, which however is easily removed. The process also enables the sulphide to be obtained at high purity.

All phase transfer catalysts are suitable as catalysts for the process according to the present invention, either free or supported on polymer matrices, and in particular ammonium salts such as trialkylmethylammonium chloride (mixture of $C_8-C_{10}$ alkyls), tricaprylmethylammonium chloride, tetrabutylammonium bromide, and phosphonium salts such as hexadecyltributylphosphonium bromide.

The use of dithiocarbonates as the starting substance is extremely advantageous in that a process has recently been devised (Synthesis, 1978, No. 5, page 365-368;

Synthesis, 1981, No. 2, page 149-151) which enables them to be produced on an industrial scale from aliphatic or arylaliphatic halides, or from methane sulphonates, from p-toluene sulphonates or from sulphates, by reaction with suitable potassium O-alkyldithiocarbonates in the presence of onium salts:

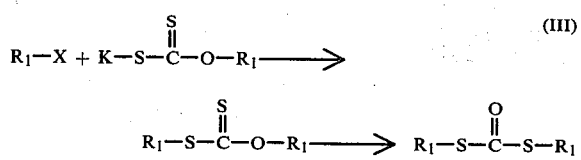

In reality, said process comprises two stages, one in which O,S-dialkyldithiocarbonates are prepared from organic halides, sulphonates or sulphates and potassium O-alkyldithiocarbonates under phase transfer conditions, and the other in which the O,S-dialkyldithiocarbonates are transposed into S,S-dialkyldithiocarbonates catalysed by onium salts under non-hydrolysing conditions. However, as both the reactions constituting process (III) are catalysed by the same onium salts, they can be carried out in succession, the first in two phases and the second by heating only the organic phase, which is normally easily separable by decantation.

It is advantageous to use process (III) for preparing the dithiocarbonates for use as starting substances in process (II) according to the present invention, because process (II) and process (III), which use the same catalysts, can in practice be carried out in succession in a single reactor.

The final separation of the R—S—$R_1$ sulphide takes place in all cases as already described, i.e. either by simple decantation or filtration, or by extraction with an organic solvent from which the sulphide is recovered by distillation or crystallisation after evaporating the solvent, or by evaporating the solvent after removing the catalyst through silica gel.

Solvents particularly suitable for extracting the final reaction mixture are light paraffin hydrocarbon fractions (petroleum ether and the like), or chlorinated solvents (trichloroethylene, carbon tetrachloride, etc.).

Some non-limiting examples of the invention are given hereinafter in order to make the process according to the present invention more easily reproducible and to demonstrate its possibility of general application.

EXAMPLE 1

Preparation of methyl octyl sulphide 2.97 grams of octyl chloride (0.02 moles) and 1.34 grams of S,S-dimethyldithiocarbonate (0.011 moles) are mixed with 0.05 grams of Aliquat 336 (tricaprylmethylammonium chloride) and 10 ml of 30% KOH.

The mixture is heated under slight reflux with energetic stirring for 15 minutes. It is cooled, extracted with petroleum ether and the solution filtered through silica gel (petroleum ether eluent) in order to eliminate the catalyst. The solution obtained is evaporated under vacuum and the residue collected. On N.M.R. and G.C. analysis (conditions: SE 30.5% on Varaport 30; programmed temperature 100° to 250° C.) the residue of 3.20 g was found to consist of pure methyl octyl sulphide.

The yield was quantitative.

A further preparation repeated in a manner identical to the preceding preparation but using 0.05 grams of hexadecyltributyl phosphonium bromide gave pure methyl octyl sulphide with a quantitative yield.

A further preparation repeated in a manner identical to the preceding preparation but using 0.03 grams of tetrabutyl ammonium bromide and in which the product was separated by simple solvent extraction, without passing the solution through silica gel, gave pure methyl octyl sulphide with a quantitative yield.

A certain number of products given in Table 1 were prepared under the same conditions as described in Example 1 (but sometimes with different catalyst quantities).

Only the variable parameters have been given for each preparation, namely the reactant proportions, the reaction time and yield.

The formed sulphides were isolated from the reaction mixture either by decantation, by filtration or by extraction with a solvent, having removed the catalyst if this was soluble in the liquid phase, either by distillation under vacuum, crystallisation or filtration through silica gel, according to the most convenient method for the particular product considered.

EXAMPLE 2

Preparation of alkylthio derivatives of chlorinated paraffins.

3.50 grams of a commercial chlorinated paraffin containing 50% of chlorine, 1.22 grams of S,S-dimethyldithiocarbonate, 0.45 grams of Aliquat 336 and 10 ml of 30% KOH, are mixed together and heated under incipient reflux with strong stirring.

The reaction is complete after 15-20 minutes.

The reaction mixture is cooled and extracted with petroleum ether. After passing the solution through silica gel, the solvent is evaporated under vacuum and leaves 3.25 grams of a chloro-methylthioparaffin containing 52% of C, 8% of H, 29% of Cl and 11% of S.

When subjected to NMR analysis, this product shows the disappearance of the band corresponding to the S,S-dimethyldithiocarbonate and the presence of the band corresponding to methylthioether groups.

TABLE 1

$R-X + (R_1-S)_2 CO \longrightarrow R-S-R_1$
 (1)           (2)                (3)

| R | X | $R_1$ | Ratio (1):(2) | Reaction time (min) | Yield % (3) | B.P. °C./tor or M.P. °C. |
|---|---|---|---|---|---|---|
| n-$C_8H_{17}$ | Cl | $CH_3$ | 1:0.55 | 15 | quant. | 97/16 |
| n-$C_8H_{17}$ | Br | $CH_3$ | 1:0.55 | 15 | quant. | 97/16 |
| n-$C_8H_{17}$ | I5 | $CH_3$ | 1:0.55 | 15 | quant. | 97/16 |
| n-$C_8H_{17}$ | $OSO_2-CH_3$ | $CH_3$ | 1:0.55 | 15 | quant. | 97/16 |
| n-$C_8H_{17}$ | $OSO_2-C_6H_4-CH_3$ | $CH_3$ | 1:0.55 | 15 | quant. | 97/16 |
| $C_6H_{13}-CH$<br>\|<br>$CH_3$ | Br | $CH_3$ | 1:0.55 | 30 | 94 | 97/23 |

TABLE 1-continued $$\underset{(1)}{R-X} + \underset{(2)}{(R_1-S)_2 CO} \longrightarrow \underset{(3)}{R-S-R_1}$$

| R | X | $R_1$ | Ratio (1):(2) | Reaction time (min) | Yield % (3) | B.P. °C./tor or M.P. °C. |
|---|---|---|---|---|---|---|
| $C_6H_5-CH_2$ | Cl | $CH_3$ | 1:0.55 | 15 | 89 | 88/15 |
| $4-O_2N-C_6H_4$ | Cl | $CH_3$ | 1:0.55 | 15 | quant. | 74-75 |
| $n-C_8H_{17}$ | Br | $C_2H_5$ | 1:0.55 | 15 | 97 | 108/16 |
| $n-C_8H_{17}$ | Br | $n-C_4H_9$ | 1:0.5 | 30 | 98 | 95/0.4 |
| $n-C_8H_{17}$ | Br | $n-C_8H_{17}$ | 1:0.5 | 30 | 98 | 152/1.5 |
| $n-C_8H_{17}$ | Br | $C_6H_5-CH_2$ | 1:0.5 | 15 | 89 | 130/0.3 |
| $n-C_8H_{17}$ | Cl | $C_6H_5-CH_2$ | 1:0.5 | 15 | 87 | 130/0.3 |
| 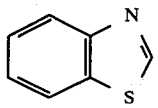 | Cl | $CH_3$ | 1:0.55 | 15 | 87 | 50-51 |

A further preparation carried out using 3.50 grams of a commercial chlorinated paraffin containing 50% of chlorine, 0.85 grams of S,S-dimethyldithiocarbonate, 0.2 grams of tetrabutylammonium bromide and 7 ml of 30% KOH, then isolating the product by simple hot decantation, gave 3.40 grams of a chloromethylthioparaffin containing 51% of C, 7% of H, 32% of Cl and 10% of S.

A further preparation, repeated in an identical manner to the preceding, but using 3.50 grams of a commercial chlorinated paraffin containing 44% of chlorine, gave 3.40 grams of a chloro-methylthioparaffin containing 53% of C, 8% of H, 29% of Cl and 10% of S.

A further preparation, repeated in an identical manner but using 3.50 grams of a commercial chlorinated paraffin containing 50% of chlorine, 1.50 grams of S,S-diethyldithiocarbonate, 0.2 grams of tetrabutylammonium bromide and 10 ml of 30% KOH, gave 3.50 grams of a chloro-ethylthioparaffin containing 54% of C, 8% of H, 26% of Cl and 12% of S. When subjected to NMR analysis, this product showed the disappearance of the bands corresponding to the S,S-diethyldithiocarbonate and the presence of the bands corresponding to the ethylthioether groups.

The products prepared in this series of tests are easily soluble in both naphthenic and paraffinic mineral oils, and in oils of both vegetable and animal origin, and gave excellent results as additives for load-bearing lubricants.

EXAMPLE 3

Preparation of 2-methylthio-4-isopropylamino-6-(3-methoxypropylamino)-s-triazine (methoprotryn)

2.60 grams of 2-chloro-4-isopropylamino-6-(3-methoxypropylamino)-s-triazine (0.01 moles), 0.98 grams of S,S-dimethyldithiocarbonate (0.008 moles), 0.25 grams of Aliquat 336 and 5 ml of 30% KOH, are mixed together and heated under strong stirring, while gradually raising the temperature to 80° C. over 15 minutes.

The initially solid mass is transformed into an oil, which is heated to 80° C. for further 15 minutes.

After this time the reaction is complete. The mixture is cooled and extracted with carbon tetrachloride.

G.C. analysis (conditions: SE 30, 5% on Varaport 30; programmed temperature 100° to 250° C.) and NMR analysis of the residue obtained by evaporating the solvent, show that the conversion to methoprotryn is quantitative.

The methoprotryn was freed from the catalyst by crystallising the crude product from petroleum ether.

The same procedure was followed for preparing a series of thioalkyl triazine derivatives, all commercially known products used as pesticides or weed killers.

Table 2 shows only the parameters which vary in the different preparations. The parameters not mentioned are always identical.

TABLE 2

$$\underset{(1)}{\underset{R_2-HN}{\overset{Cl}{\underset{N}{\parallel}}} \underset{N}{\overset{N}{\underset{NH-R_3}{}}}} + (R_1-S)_2 CO \longrightarrow \underset{(3)}{\underset{R_2-HN}{\overset{S-R_1}{\underset{N}{\parallel}}} \underset{N}{\overset{N}{\underset{NH-R_3}{}}}}$$

| (3) | $R_2$ | $R_3$ | $R_1$ | Ratio (1):(2) | Reaction time (min) at 80° C. | Yield (%) | M.P. °C. of (3) (crystallisation solvent) |
|---|---|---|---|---|---|---|---|
| Simetryne | $C_2H_5$ | $C_2H_5$ | $CH_3$ | 1:0.8 | 20 | quant. | 82-84 (bz.-pet. et.) |
| Ametryn | $C_2H_5$ | $i-C_3H_7$ | $CH_3$ | 1:0.8 | 30 | quant. | 87-89 (bz.-pet. et.) |
| Terbutrina | $C_2H_5$ | $t-C_4H_9$ | $CH_3$ | 1:0.8 | 15 | quant. | 115-117 (bz.-pet. et) |
| Prometryn | $i-C_3H_7$ | $i-C_3H_7$ | $CH_3$ | 1:0.8 | 20 | 93 | 123-124 (bz.-pet. et.) |
| Methoprotryn | $i-C_3H_7$ | $(CH_2)_3-OCH_3$ | $CH_3$ | 1:0.8 | 15 | 97 | 70-71 (pet. et.) |
| Dipropetryn | $i-C_3H_7$ | $i-C_3H_7$ | $C_2H_5$ | 1:0.8 | 30 | 89 | 102-104 (bz.-pet. et.) | bz. = benzene
pet. et. = petroleum ether

We claim:
1. A process for preparing organic sulphides of formula:

R—S—R$_1$ in which: R is an aliphatic, aryl, arylaliphatic or heterocyclic radical, and R$_1$ is an aliphatic or arylaliphatic radical, characterized by reacting organic dithiocarbonates with an alkylating or arylating agent in the presence of an aqueous alkaline base and a phase transfer catalyst, at a temperature of about 50° to 100° C., in accordance with the equation:

$$2R\text{—}X + (R_1S)_2CO + H_2O \rightarrow 2R\text{—}S\text{—}R_1 + 2HX + CO_2 \quad (I)$$

in which R and R$_1$ are as heretofore defined, and X is Cl, Br, I, —SO$_3$CH$_3$, or —SO$_3$—C$_6$—H$_4$—CH$_3$.

2. A process as in claim 1, wherein the aqueous alkaline base is 30% KOH or NaOH.

3. A process as in claim 1, wherein the phase transfer catalyst is an ammonium or phosphonium salt.

4. A process as in claim 1, wherein if the catalyst used is water-soluble, the organic sulphide is separated from the reaction mixture by simple decantation.

5. A process as in claim 1, wherein if the catalyst used is soluble in the organic phase, the organic sulphide is freed from the catalyst by extraction with an organic solvent followed by evaporation of the solvent and subsequent distillation under vacuum or subsequent crystallisation.

6. A process as in claim 1, wherein if the catalyst used is soluble in the organic phase, the organic sulphide is freed from the catalyst by extraction with an organic solvent, then passing the solution through silica gel, followed by evaporation of the solvent.

7. A process as in claim 1, wherein the reaction mixture is heated for 10–60 minutes.

* * * * *